United States Patent
Kieft et al.

(10) Patent No.: US 9,724,052 B2
(45) Date of Patent: Aug. 8, 2017

(54) DOCTOR AWARE AUTOMATIC COLLIMATION

(71) Applicant: KONINKLIJKE PHILIPS N.V., Eindhoven (NL)

(72) Inventors: Erik René Kieft, Eindhoven (NL); Bart Pierre Antoine Jozef Hoornaert, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 232 days.

(21) Appl. No.: 14/422,763

(22) PCT Filed: Aug. 9, 2013

(86) PCT No.: PCT/IB2013/056528
§ 371 (c)(1),
(2) Date: Feb. 20, 2015

(87) PCT Pub. No.: WO2014/033573
PCT Pub. Date: Mar. 6, 2014

(65) Prior Publication Data
US 2015/0245804 A1    Sep. 3, 2015

Related U.S. Application Data

(60) Provisional application No. 61/693,378, filed on Aug. 27, 2012.

(51) Int. Cl.
*G21K 1/04* (2006.01)
*A61B 6/06* (2006.01)
(Continued)

(52) U.S. Cl.
CPC ............ *A61B 6/06* (2013.01); *A61B 6/107* (2013.01); *A61B 6/4441* (2013.01); *A61B 6/542* (2013.01);
(Continued)

(58) Field of Classification Search
CPC ......... A61B 6/06; A61B 6/4441; A61B 6/584; A61B 6/542
(Continued)

(56) References Cited

U.S. PATENT DOCUMENTS 6,055,295 A       4/2000  Murthy et al.
6,501,820 B2 *  12/2002  Guendel ................ A61B 6/032
                                                              378/15
(Continued)

FOREIGN PATENT DOCUMENTS

WO        2012123850 A1      9/2012

OTHER PUBLICATIONS

Geeta et al, "Radiation Exposure to the Patient and Operating Room Personnel During Percutaneous Nephrolithotomy", International Urology and Nephrology, vol. 38, No. 2, XP019409753, 2006, pp. 207-210.

(Continued)

*Primary Examiner* — Courtney Thomas

(57) ABSTRACT

A controller and a related method of controlling a collimator. The controller operates to select a collimator setting for collimator of an x-ray imager for acquiring an image of a ROI in a patient. The controller operates to select the collimator setting to optimize the patient dosage in respect of primary radiation and secondary radiation dosage of medical staff. A position detector supplies to the controller a current position of a person relative to a patient. Based on said supplied position, the controller's configured to perform an optimization procedure that takes into account the staff dosage in respect of the secondary radiation dosage to reduce the secondary radiation dosage.

17 Claims, 5 Drawing Sheets

(51) Int. Cl.
*A61B 6/10* (2006.01)
*A61B 6/00* (2006.01)

(52) U.S. Cl.
CPC .............. *A61B 6/584* (2013.01); *A61B 6/486* (2013.01); *A61B 6/503* (2013.01)

(58) Field of Classification Search
USPC .................................................. 378/147–153
See application file for complete search history.

(56) References Cited

U.S. PATENT DOCUMENTS

| | | |
|---|---|---|
| 7,016,453 B2 | 3/2006 | Ruimi |
| 7,340,033 B2 | 3/2008 | Mollus et al. |
| 7,539,284 B2 | 5/2009 | Besson |
| 2006/0104420 A1 | 5/2006 | Mollus |
| 2007/0128636 A1 | 6/2007 | Baker et al. |
| 2011/0075805 A1 | 3/2011 | Machan et al. |

OTHER PUBLICATIONS

Den Boer et al, "Reduction of Radiation Exposure While Maintaining High-Quality Fluoroscopic Images During Interventional Cardiology Using Novel X-Ray Tube Technology With Extra Beam Filtering", Circulation 89, Journal of the American Heart Assosciation, 1994, pp. 2710-2714.

* cited by examiner

# DOCTOR AWARE AUTOMATIC COLLIMATION

CROSS-REFERENCE TO PRIOR APPLICATIONS

This application is the U.S. National Phase application under 35 U.S.C. §371 of International Application Serial No. PCT/IB2013/056528, filed on Aug. 9, 2013, which claims the benefit of U.S. Application Ser. No. 61/693,378, filed on Aug. 27, 2012. These applications are hereby incorporated by reference herein.

FIELD OF THE INVENTION

The present invention relates to a collimator controller, to a collimator control method, to an x-ray imager system, to a computer program element and to a computer readable medium.

BACKGROUND OF THE INVENTION

X-ray beam collimation is an important procedure in x-ray imaging.

Proper collimation of the x-ray beam to a region of interest helps keep patient radiation dosage down and improve image quality. Automatic collimation has been developed in the past to make operation of x-ray imagers easier. In automatic collimation an x-ray imager's collimator configuration is adjusted with minimal or no user interaction.

U.S. Pat. No. 2 7,340,033 describes a type of automatic collimation.

However it has been observed that medical staff who are present during imager's operation are exposed to quite significant dosages even though good collimation has been achieved.

SUMMARY OF THE INVENTION

There may therefore be a need for an alternative apparatus to effect collimation of an x-ray beam for imaging purposes.

The object of the present invention is solved by the subject matter of the independent claims where further embodiments are incorporated in the dependent claims. It should be noted that the following described aspect of the invention equally apply to the collimator control method, the x-ray imager system, to the computer program element and to the computer readable medium.

According to a first aspect of the invention there is provided a collimator controller configured to select, from at least two different collimator settings, a collimator setting for an x-ray imager to acquire an image of an object whilst a person is present at a position in a vicinity around said object, each setting defining i) a target volume of the object to be irradiated by a beam of primary radiation generated by an x-ray source of said imager and ii) a non-target volume of the object not to be irradiated by said primary radiation beam or to be irradiated at lesser intensity than the target volume, the controller's selection biased for the one of the at least two settings that results in a longer path length through the object for the secondary radiation along a direction between the target volume and the position of the person, if each of the at least two collimator settings cause about the same dosage for the object when so irradiated.

According to one embodiment the controller's selection operation is based on a weight attached to at least one part of the target volume of the object, wherein the weight attached to said part is non-zero, said weight generally reflecting the path length through the object for the secondary radiation along a direction between said part and the position of the person, said weight effecting said bias, the so selected collimator setting, when used by the imager, resulting in a lower secondary radiation dosage for the person compared to at least one of the at least one other collimator setting. In one embodiment, the weight or weights are chosen to favor collimator settings that result in longer path lengths.

In one embodiment the object is a human or animal patient and the person may be attending medical staff such as an interventional radiologist carrying out an intervention (such as PCI or similar) on the patient and is therefore in relative close proximity to the patient during imaging. Secondary (or scatter) radiation dosage can be reduced for medical staff because from the two or more collimator settings affording a similarly (low) primary radiation dosage to the patient, the instant controller selects the one where the patient's body itself would serve as a better scatter radiation blocker or filter because a larger fraction of the patient's body is situated between the volume of interest or the region that would be the case for competing or other collimator settings. The collimator controller examines the target volumes of a set of collimator settings that each includes the region of interest and then returns the collimator setting whose target volume is "shifted/removed away" as far as possible from the radiologist's position. An additional physical secondary radiation barrier may not be needed.

According to one embodiment, the weights are attached to the target volume only. The weights vary as a function of the path length of secondary radiation through the patient's body (target volume as well as non-target volume) towards the radiologist's position. The weights vary (quasi) continuously as a function of position in or of the target volume.

According to one embodiment the controller further includes a detection unit configured to detect the operator's position relative to the object.

According to one embodiment the detection unit including a position sensor integrated in a badge wearable by the operator.

According to one embodiment the detection unit including at least one actuator device arranged at a predefined position at the imager, the actuator device actuatable by the operator to specify that the operator's position is substantially equal to said predefined position.

According to one embodiment the detection unit including a graphical user interface comprising at least one graphical input button associated with a pre-defined position relative to the imager or the object, the button actuatable by the operator to specify that the operator's position is substantially equal to said predefined position.

According to one embodiment the detection unit includes a range camera operable to sense the operator's position.

According to one embodiment the controller configured to vary the weight attached to parts or volume elements of the target volume as a function of the detected operator distance to the object. This allows to gradually mitigate controller' selection bias with increasing physician-radiologist distance. The bias which is to reduce secondary radiation dosage of the radiologist is gradually faded out, that is, becomes less and less prominent with increasing radiologist-patient distance and conversely becomes stronger the smaller the physician-patient distance. This is to account for the fact that the scatter or secondary radiation dosage becomes more and more irrelevant as the patient-radiologist distance becomes larger. Radiologist-patient distance is measured according to one embodiment relative to the region of interest in the patient.

According to one embodiment, if the radiologist's distance from patient exceeds a user-definable critical distance, the bias is disabled and controller's optimization or selection is then only concerned with patient dosage and no more regard is had to secondary radiation dosage on physician.

According to one embodiment the controller configured to vary the weight attached to the part as a function of the direction of the primary radiation. This allows further adjusting the weighting used to the particular projection direction used by the imager for a given image acquisition.

The invention can be applied in any X-ray intervention that uses automatic collimation. In particular, it can be used in applications where medical staff receives relatively high radiation doses due to the large number of procedures they perform.

The controller's biasing function can be included as an add-on to existing collimation optimizers.

BRIEF DESCRIPTION OF THE DRAWINGS

Exemplary embodiments of the invention will now be described with reference to the following drawings wherein:—

DETAILED DESCRIPTION OF EMBODIMENTS

Figure 1:
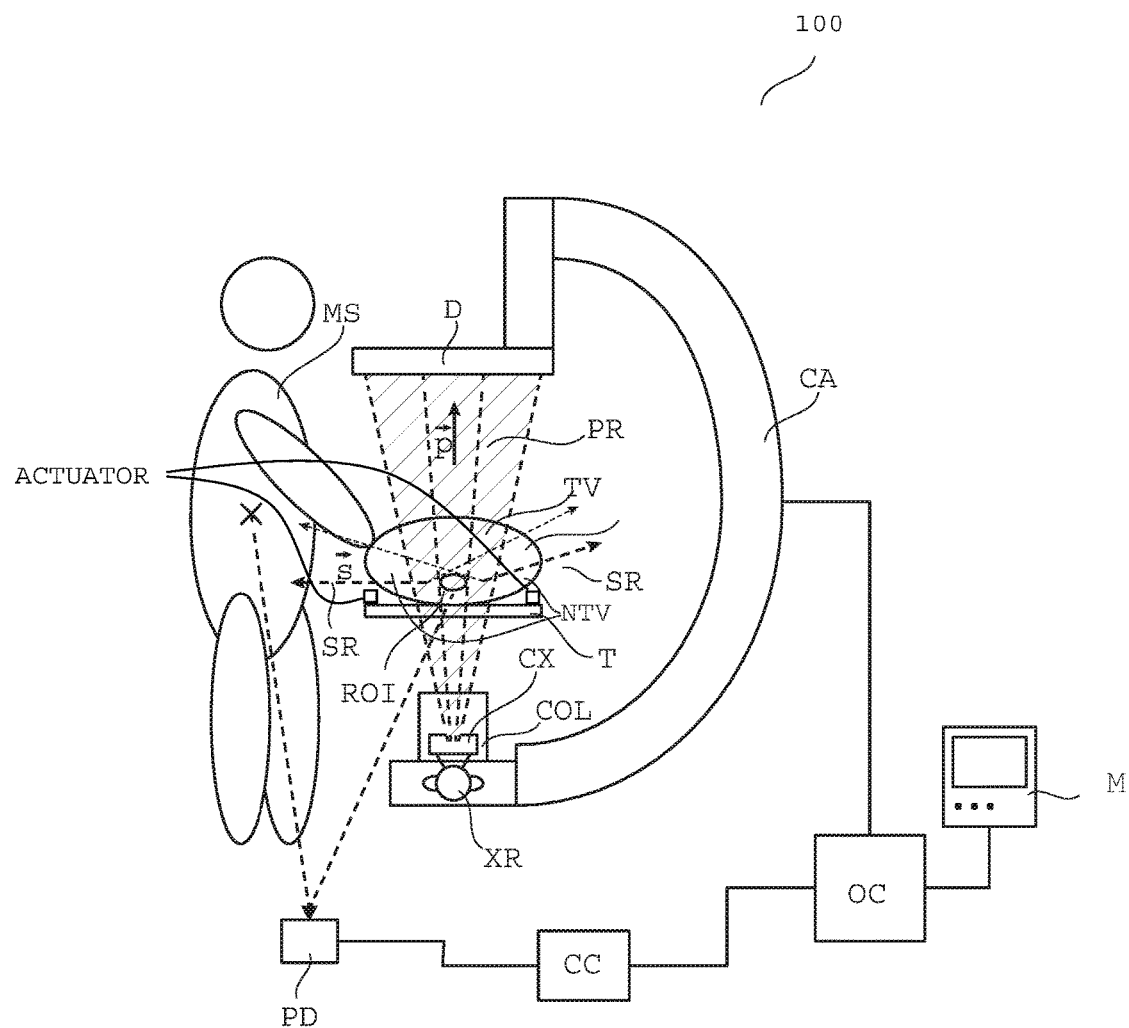
FIG. 1 shows an imager arrangement.

In FIG. 1 there is shown an imager arrangement according to one embodiment.

There is an x-ray imager 100 of the C-arm type as frequently used for interventional procedures. An example of such interventional procedures is PCI (percutaneous coronary interventions) where a medical device such as a stent is introduced into patient PAT and navigated by an interventional radiologist MS (hereinafter referred to as "radiologist" or "medical staff" or "operator" or "person") through appropriate vessels to a lesion site. X-ray projection images are taken of patient PAT during the intervention and the images are displayed on a screen M by the x-ray imager 100 to help radiologist MS navigate the medical device.

Imager 100 includes a rigid C-arm CA having affixed thereto at one of its ends a detector D and to the other a housing CX which houses an x-ray tube XR and a collimator COL (hereinafter together referred to as the C-X-assembly). X-ray tube XR operates to generate and emit a primary radiation x-ray beam PR whose main direction is schematically indicted by vector p. As will be explained in more detail below with reference to FIG. 2, collimator COL operates to collimate said x-ray beam.

The C-arm construction allows the radiologist MS to stay very close to the patient PAT at virtually any desired position around the patient called for by medical necessity whilst carrying out the intervention and whilst the projection images are acquired. The position of the arm CA is adjustable so that the projection images can be acquired along different projection directions p. The arm CA is rotatably mounted around an examination table T on which patient PAT lies during the intervention and during the imaging. The arm CA and with it the CX assembly is driven by a stepper motor or other suitable actuator.

Overall operation of imager 100 is controlled by operator from a computer console OC. Console OC is coupled to screen M. Operator can control via said console OC any one image acquisition by releasing individual x-ray exposures for example by actuating a joy stick or pedal or other suitable input means coupled to said console OC.

During the intervention and imaging examination table T (and with it patient PAT) is positioned between detector D and x-ray tube XR such that the lesioned site or any other related region of interest ROA is irradiated by primary radiation beam PR.

Broadly, during an image acquisition the collimated x-ray beam PR emanates from x-ray tube XR, passes through patient PAT at said region ROI, experiences attenuation by interaction with matter therein, and the so attenuated beam PR then strikes detector D's surface at a plurality of the detector cells. Each cell that is struck by an individual ray (of said primary beam PR) responds by issuing a corresponding electric signal. The collection of said signals is then translated by a data acquisition system ("DAS"—not shown) into a respective digital value representative of said attenuation. The density of the organic material making up the ROI, for example rib cage and cardiac tissue in case of a PCI, determines the level of attenuation. High density material (such as bone) causes higher attenuation than less dense materials (such as the cardiac tissue). The collection of the so registered digital values for each (x-)ray are then consolidated into an array of digital values forming an X-ray projection image for a given acquisition time and projection direction.

Now, in order to acquire the x-ray image, the imager 100 needs first to be aligned to said region of interest ROI by adjusting c-arm CA position relative to patient PAT and by adjusting table T height. This defines the imager's geometry.

With continued reference to FIG. 1, apart from the primary radiation beam PR there is also, undesirably but unavoidably, secondary radiation SR that results from Compton interaction of primary radiation with patient tissue. Secondary radiation SR spreads, in particular, sideways around patient PAT as indicated in FIG. 1 by vector s and across the examination room and is incident in particular on nearby radiologist MS positioned somewhere near patient PAT to carry out the intervention.

Prior to the actual image acquisition primary beam radiation PR is collimated to the desired ROI. This is achieved by Collimator COL when properly adjusted. Primary x-ray radiation PR generated by x-ray tube XR egresses same, ingresses collimator C and egresses as a collimated primary radiation beam PR shown as a hachured cross-sectional cone in FIG. 1. It is understood that the actual geometry that is the shape of the beams' horizontal cross-section (formed by a horizontal plane thought to intersect said beam) is a matter of the collimator's construction and could be rectangular (as it indeed is according to the embodiment of FIG. 2) or circular or any other curvilinear shape. An objective in collimation is to adapt primary radiation beam PR's horizontal cross-section to the outlines of the region of interest ROI. Prior to collimator interaction, primary x-ray beam PR egressing x-ray tube XR (in projection direction p) is a divergent beam so in absence of collimator COL the cross-sectional dimensions of the beam p when reaching patient PAT would be much larger than the area of the desired ROI.

This is unsatisfactory because patient dosage may have to be increased unnecessarily which in turn causes even more Compton scatter to occur. The purpose of collimator COL or "beam restrictor" is to restrict dimensions of the cross section of the beam PR so as to match in size and shape the beam PR's cross section to that of the region of interest ROI.

Figure 2:
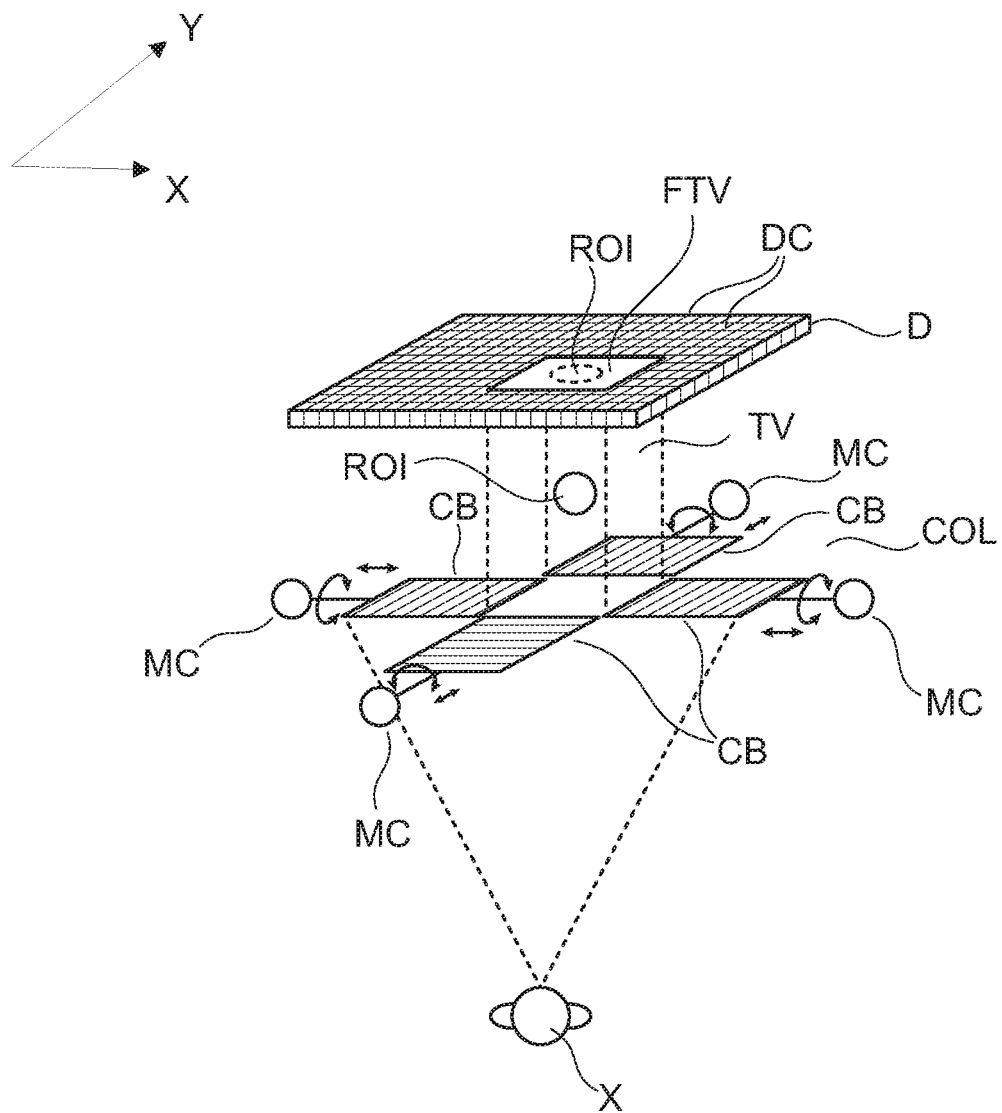
FIG. 2 shows a collimator arrangement used in FIG. 1.

With reference to FIG. 2 an embodiment of collimator COL is shown in cut away view where the detector D's surface and detector cells DC are visible from above in a direction opposite to x-ray beam PR's direction of travel.

Collimator COL comprises two pairs of blades CB or sheets ("shutters") formed from lead or tungsten or other highly radiation-opaque material. One pair is arranged perpendicularly to the other and the blades are individually addressable and movable by a respective collimator stepper motor MC so as to restrict more or less the beam in either or two of the two dimensions depending on their relative position. Blades CB may be rotatable and/or shiftable as shown by curved and straight arrows, respectively. In this way the beam PR's cross section can be shaped to match the expected two dimensional outline of the region of interest ROI. The collimator arrangement in FIG. 2 allows shaping the beam into square or rectangular forms in various sizes. In another embodiment a multi-leaf collimator is used comprising instead of the four blades a large number of motor-movable slats or strips arranged in opposing relationship. A multi-leaf collimator allows forming more detailed or curvilinear shapes.

Setting up the collimator COL amounts to determine how to position the blades so as to make the resulting beam cross section match the perimeter of the ROI as close as possible. In the four blade collimator embodiment, the matching of said rectangular shape to the ROI is achieved by determining blade positions for each blades CB. When the blades are energized to assume the determined positions they together define an aperture with which the smallest or a reasonably small rectangular beam cross section can be realized that still includes all of the desired ROI.

In one embodiment collimator COL additionally includes movable "wedges" (not shown) made from brass sheet or other non-radiation-opaque material that can be slid into position also to further restrict the aperture formed by the blades BC. Said wedges are likewise movable by stepper motors. Interposing said wedges make part of beam PR impact patient PAT at lesser intensity than the remaining part of beam PR. The sheet from which the wedges are formed have a vertical thickness that decreases from its center to its edges. Sliding in the wedges allows smoothing the radiation intensity drop around the apertures edge. Because of the gradually decreasing thickness, the degree of said smoothing can be fine-tuned by gradually moving wedges into position.

Operation of said stepper motors MC for blades or wedges is controlled by console OC issuing corresponding control signals to position each of the blades or wedges according to manually or automatically set collimator setting parameters. Console OC runs suitable driver software and includes suitable interface units to interface with collimator COL.

Each collimator setting or configuration corresponds to a specific position of blades BC or wedges forming the collimator aperture shown in FIG. 2 bounded the four blades. Because of the high radiation opacity of blades CB, primary radiation beam PR incident on the blades CB is blocked whereas that part of radiation beam PR that is directed at the aperture is not blocked so can pass collimator COL to irradiate patient PAT volume in a target volume TV.

The primary radiation PR is attenuated after passage through target volume TV and so attenuated primary radiation x-ray beam PR is then incident on detector D's detector cells DC. The collection of responding detector cells DC in detector D's image plane form a projection image or "footprint" FTV of said target volume TV. A boundary of said target volume footprint FTV can be defined in terms of pixel coordinates by a 2-dimensional closed curve $C_{x,y}$ ("collimator curve"). Each pixel inside or on the curve is a projection of a point in patient target volume TV. In other words, each collimator setting corresponds to such a curve $C_{x,y}$. Although not every plane curve corresponds to a collimator setting, a restriction to a suitable family of plane curves does. The restriction depends on the type of the collimator. For instance the collimator settings of 4-blade collimator shown in FIG. 2 can be defined in terms of rectangular curves $C_{x,y}$. In other words when restricting to rectangular plane curves, there is a one-to-one correspondence between rectangular curves $C_{x,y}$ and the set of realizable collimator settings.

It follows from the above, that each collimator setting defines its respective target volume TV and conversely, said respective definition of target volume TV defines a respective non-target volume NTV. The non-target volume NTV is the remainder of the patient's body through which no (or at lesser intensity) primary radiation path PR is supposed to pass.

Different collimator settings can be chosen (that differ in size and position) so that their respective target volumes TV include the region of interest ROI. The ROI can be specified by image coordinates for instance by a manual or automatic segmentation in an image registered onto the current imager's geometry and patient PAT position.

The space of all suitably restricted curve $C_{x,y}$ (which may be other than rectangular for different collimator types) that each include the specified ROI will be referred to hereafter as the "phase space" of (all realizable) collimator settings.

Referring back to FIG. 1, the arrangement includes a collimator controller CC communicatively coupled to a position detector or sensor PD. The collimator settings of collimator COL are automatically controlled by collimator control CC. The control operation is automatic in the sense that the parameters for the blade CB and/or wedge positions are computed by controller CC and need not be supplied by the operator and controller CC then applies corresponding control signals to collimator COL to adjust its blade settings accordingly.

Given a specific projection direction p for primary radiation PR as defined by the C-arm position relative to a patient PAT, controller CC is programmed to compute based on a coordinate or otherwise description of the region of interest ROI an optimized collimator setting. The setting is optimal so as to keep the x-ray dosage on the patient low given a desired image quality/contrast. But unlikely previous collimation optimizers, the collimator control CC as proposed herein not only optimizes collimator settings in respect of patient radiation dosage caused by primary radiation beam PR directed at patient PAT but it also takes into account x-ray dosage on medical staff MS incurred by the secondary radiation SR caused by primary radiation PR. To this end, a position detector PD operates to detect a current position of medical staff MS relative to patient PAT. Said position is translated into a line with direction from patient PAT to medical staff ("patient-doctor direction" or "patient-doctor line") which is then used to compute the collimator stetting as will be explained in more detail below with reference to FIG. 4.

The collimator controller CC as proposed herein harnesses an observation of a geometro-radiological situation which will now be explained with reference to FIG. 3a and b. Each of FIG. 3a,b shows projection images 305 and 310 acquired along projection direction p but each with a different collimator setting. Shadows (shown in dark grade shadings) of collimator blades or wedges interposed between x-ray source and patient PAT are shown in FIG. 3. The projection view FTV on the target volume TV (shown in lighter grade shadings in FIG. 3a,b) is generated by the primary radiation PR that passed through the collimator's core aperture and was therefore not blocked by the blades CB. Target volume footprint FTV includes footprints of the ROI which in the example of FIG. 3a,b show segmented portions of a guide-wire used in the intervention by radiologist MS.

Figures 3A, 3B:
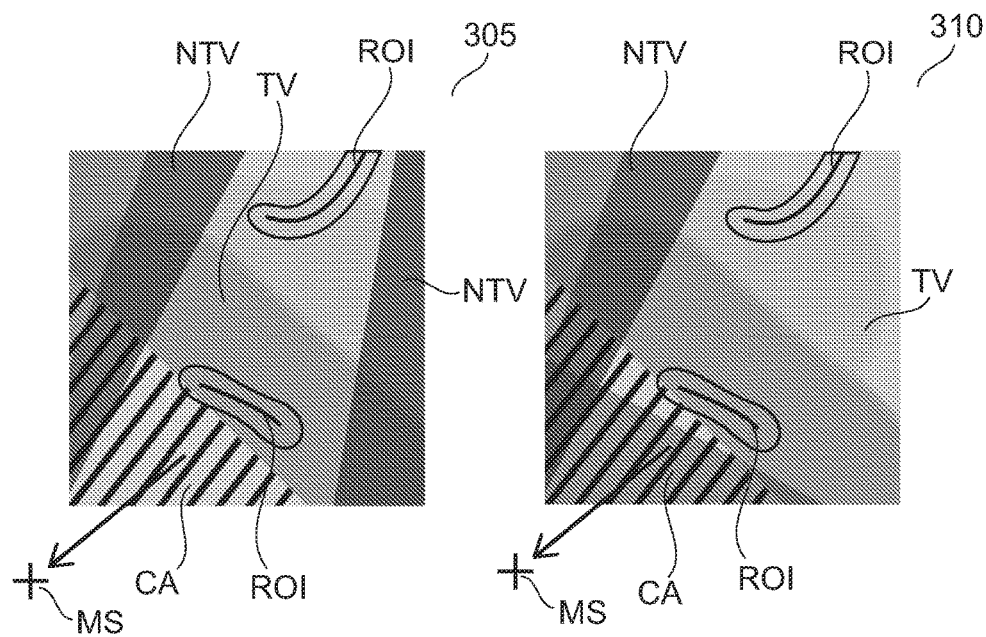
FIG. 3 shows projection images obtained by collimating an x-ray beam.

The two collimator settings in FIG. 3a,b differ in that in FIG. 3b a critical area CA at the lower edge of the image is now next to completely blocked out. As compared to FIG. 3a, one of the blades BC moved in from below in y-direction so blade CB's shadow or footprint now covers most of the striped triangular area that represents said critical patient volume CA. The arrow at the lower left hand corner in each image shows the direction from the target volume TV towards the position of medical staff indicated by a cross hair MS.

In both collimator settings 3a and 3b patient dosage is about the same because in each case the respective target volumes TV are about the same (assuming that radiation absorption is about the same on average across both areas). Yet from the medical staff MS point of view, collimation setting according to FIG. 3a is less preferable because medical staff MS are exposed to a higher dosage of secondary radiation SA. This is where the criticality of critical area CA comes into play. As the geometry in both FIG. 3a,b show, the critical area CA is proximal in respect to operator MS's position. Therefore, irradiating said critical area CA according to collimator setting of FIG. 3a would cause said proximal volume CA to generate secondary radiation to which the operator would be exposed to. This is unlike the situation for collimator setting in FIG. 3b where the critical area CA is now not irradiated by primary radiation PR so the critical area CA now actually serves as a radiation barrier or a filter for secondary radiation SR generated at the now, with respect to medical staff MS position, more distal target volume TV. In other words, target volume TV where primary radiation PR is impacting (to cause undesirable secondary radiation SR) can be thought to have been "shifted away" from medical staff MS's position when the collimator setting according to FIG. 3b is chosen rather than according to FIG. 3a.

In yet other words the FIG. 3b collimator setting is preferred because in both collimator settings:—
i) the same patient dosage is incurred,
ii) primary radiation PR irradiates the region of interest ROI, but still
iii) medical staff MS would be exposed to less secondary radiation SR.

Collimator control CC as proposed herein is programmed to compute based on a given ROI position and a given medical staff MS position a collimator setting. The computation or selection of said collimator setting includes an optimization step that is geared to find the collimator setting that would yield a primary radiation dosage for the patient close as possible to the minimum but said step is at the same time biased to favor the solution in FIG. 3b over the solution in FIG. 3a. The relatively small shift of the collimator's focus area away from current medical staff MS position can still result in a significant reduction of secondary radiation dosage. It may be recalled here that roughly every 3 cm of additional tissue between the irradiated volume TV and staff position MS will reduce the scattered secondary radiation dosage by a factor of 2. Medical staff MS who carry out a large number of interventions per year can therefore expect a significant cutting down of their annual dosages.

The operation of collimator controller CC will now be explained in more detail.

Operation

Controller CC receives as input a specification of the ROI. According to one embodiment operator MS inputs via a GUI display on screen M or other suitable input means such as a pointer tool or keyboard said ROI specification. A user interface front-end translates this request into a coordinate description such as a binary mask or otherwise that is mapped to the detector cells CD of detector D.

Controller CC further receives as input a current position of staff MS supplied by position detector or sensor PD. Position detector is configured to detect or sense radiologist's MS position relative to the patient and/or x-ray imager 100 and/or examination table T. Position detector PD operates manually or automatically.

According to one embodiment position detector PD includes a user interface that affords to medical staff MS to manually select their position via a touch screen or via a combination of keystrokes on the keyboard. For example operator MS may indicate his or her position by choosing "left side" and "right side" of the table with respect to patient's longitudinal axis along either one of the two directions. More detailed specification or resolution of staff position such a "cranial left, "cranial right", "left upper quadrant", "right upper quadrant", "left lower quadrant", "right lower quadrant" etc. are envisaged also in some embodiments.

According to one embodiment, there are actuators such as buttons arranged on each side of the patient table. Staff MS indicates to controller CC their position by actuating the button closest to them when assuming the appropriate position called for by the intervention to be carried out.

According to one embodiment, position detector PD operates automatically. More specifically and according to one embodiment, position sensors are integrated in dose badges that are worn by staff MS. This has the advantages that a plurality of staff members, as well as their respective distances from the X-ray system can be taken into account to give less priority to staff dose when staff is at a greater distance than others. This embodiment will be explained in more detail below.

According to one embodiment, position detector includes a time-of-flight or 3D range camera to detect position of medical staff MS in examination theater (cathlab).

In yet another embodiment, position sensors are integrated in the edges of the examination table and operate to supply a stream or feed of updated positions of the radiologist as he or she moves about the patient carrying out the intervention.

Because the imager 100's geometry is assumed to be known the detected position of the physician can be translated into a position relative to the target volume TV for any given collimator setting. The directed patient-doctor line can then be defined by using a reference point of ROI (for example its centroid or a center or gravity or other descriptors may be computed) and the staff position MS received from detector PD. This line can be defined by choosing reference points with respect to each, region of interest ROI and staff position as detected by position detector PD.

The critical area CA can then be defined as the half-plane tangent to segmented ROI's boundary with the patient-doctor line as said half-plane's normal. In other words critical area CA is that part of patient PAT volume that lie in said half plane so is proximal to doctor position PD relative to the ROI. Referring back to FIG. 3a,b, the striped triangular plane portion is a section of said critical area CA's projection.

Controller CC runs an optimizer algorithm that iterates through the phase space of possible collimator settings. This can be done by iterating through parameters parameterizing the 2-dimensional curves $C_{x,y}$ definable on the detector D image plane and outlining a possible target volume FTV footprint. As mentioned above, each curve C corresponds to a collimator setting. The parameters are varied to find the one or more curves that would yield a low patient dosage whilst considering the secondary radiation dosage on physician MS that this setting would incur based on radiologist MS's detected position.

Unlike previous automatic collimation optimizer algorithms, the algorithm used by controller CC attaches, for any collimator setting it is iterating through, a higher weight to those parts of the x-ray beam PR that would irradiate the critical area CA. Given the detected position of the radiologist relative to the region of interest ROI, those collimator settings whose target volume TV is proximal to the radiologist attracts a higher penalty in the optimization algorithm than collimator setting whose target volume TV is more distal to the radiologist. The proximal part is the critical CA area introduced earlier in FIG. 3. According to one embodiment the CA area or volume is that part of the patient volume through which the "patient-doctor" line directed from ROI to radiologist MS passes.

Controller CC's optimizer operates to optimize an objective function FoM (Figure of Merit):

$$FoM = \alpha \cdot FoM_{patient} + \beta \cdot FoM_{staff} \quad (1)$$

The common objective function FoM comprises two competing functions $FoM_{patient}$ and $FoM_{staff}$.

$FoM_{patient}$ may represent a conventional figure of merit for automatic collimation, typically a number that scales with patient DAP (dose area product) rate. Stated differently, conventional automatic collimation is represented by $\alpha=1$, $\beta=0$ so that $FoM=FoM_{patient}$. $FoM_{patient}$ relates only to primary radiation dosage.

The other objective function $FoM_{staff}$ is different from $FoM_{patient}$ and attempts to optimize staff dose instead of patient dose. In other words $FoM_{staff}$ weighs different parts of the patient body differently (from $FoM_{patient}$'s weighing) depending on their potential contribution to scattered irradiation SR directed to staff position as detected sensor PD.

Expressed in image coordinates in detector D's image plane, when the direction towards the doctor is known as shown in FIG. 3, the weights of the pixels in the image plane depend on their distance to the doctor, with the weights varying with distance to detected staff position. That is, the closer any pixel to the "doctor" the higher the weight. The dependence on distance can be configured to vary exponentially in one embodiment to so mimic the absorbing effect of patient tissue for scattered radiation SR.

For 'doctor aware' automatic collimation as proposed herein, a non-zero weighting factor $\beta>0$ is set. The ratio between weighting factors $\alpha$ and $\beta$ determines how strongly staff dose is considered in optimizing the automatic collimation.

In one embodiment, the value of $\beta$ can be fixed in the system or is manually configurable by the user, but it can also be made automatically dependent on any one or a combination of the following factors:

I) $\beta \ll \alpha$ when the doctor is outside the examination room or behind a lead screen;

II) $\beta$ as a function of the distance from the c-arm CA to the nearest radiologist from a plurality of radiologist;

III) $\beta$ as a function of how far the irradiated volume TV on the patient is from the radiologist's side of the patient PAT (See FIG. 4);

IV) $\beta$ as a function of the c-arm CA position/projection direction p, e.g. $\beta$ is high in LAO (left anterior oblique) orientation and $\beta$ is low in RAO (right anterior oblique) orientation when the doctor is at the right hand side of the patient.

Put differently, when multiple collimator positions exist that are nearly similar in terms of patient dose, doctor aware automatic collimation (with a properly selected value of $\beta$) favors or is biased to returning a collimator setting that results in significantly reduced staff dose, with similar or only slightly higher patient dose compared to a collimator setting that a conventional (that is, a purely patient dosage focused) automatic collimation optimizer would have returned.

FoM is a function on the phase space of collimator settings, that is, is a function of closed curves $C_{x,y}$ in detector D's image plane as explained earlier above in relation to FIG. 3.

Controller CC minimizes $$FoM(C_{x,y}) = \underset{C_{x,y}}{\operatorname{argmin}}[\alpha \cdot FoM_{patient}(C_{x,y}) + \beta \cdot FoM_{staff}(C_{x,y})]$$

$\beta \cdot FoM_{staff}(\bullet)$ may be considered a penalty function for $\alpha \cdot FoM_{patient}(C_{x,y})$.

In one embodiment, $FoM_{patient}(C_{x,y})$ is defined as the area target volume footprint FTV onto detector plane D, $FoM_{patient}(C_{x,y}) = \iint_{FTV} dA$ where A represents the area of the projection. In this approximation, each part of the footprint FTV contributes equally to patient DAP (dose area product) rate.

In one embodiment, $FoM_{staff}(C_{x,y})$ is defined as the area of overlap of the projections of the critical area CA and the target volume footprint FTV onto the detector plane, $\iint_{FTV \cap CA} dA$. In this embodiment any overlap between the critical area and the target volume of a collimator setting is penalized. In this embodiment, $\beta$ may be chosen a constant and the ratio between constant $\alpha$ and $\beta$ determines how strongly the bias should come to be considered in the selection.

In another embodiment, $FoM_{staff}(C_{x,y})$ integrates over the complete area of the FTV, but with an additional weight representing the path length of secondary radiation through the patient, $FoM_{patient}(C_{x,y}) = \iint_{FTV} \exp(-d(pixel)/d_0) dA$, where d(pixel) is the distance from the respective part of the volume to the (estimated) boundary of the patient in the direction of the doctor, and $d_0$ is a constant.

According to one embodiment $$\beta \sim \frac{1}{dist(C_{x,y}, pos(MS))}$$

where dist($C_{x,y}$, pos(MS)) is defined as the path length ("patient-doctor path length") of the patient-doctor line, that is, the distance on said line between radiologist MS's position and the curve $C_{x,y}$ of the respective collimator setting. The distance in respect of collimator setting curve $C_{x,y}$, can be measured by the respective reference point of the ROI as each collimator curve is required to circumscribe the ROI as defined earlier. Alternatively, a separate reference point for the collimator setting curve can be defined as the centroid or center of gravity of the closed curve $C_{x,y}$. This definition of β can be used with either embodiment of $FoM_{staff}$ above instead of choosing β a constant.

In either embodiment above, the definition for $FoM_{staff}$ is so chosen that collimator controller CC's operation is biased to return collimator setting curves that result in longer patient-doctor line path lengths. In other words, for two competing collimator settings resulting each in about the same patient dosage, the one with the longer patient-doctor path length will be returned.

According to one embodiment, position detector PD is configured to individually capture respective positions of a plurality of radiologists. In one embodiment, each radiologist has an individual position transponder that can be interrogated by position detector PD. In one embodiment, said transponders are integrated in the dosage badges of each radiologist. In case of multiple radiologist positions, controller CC is configured to operate in one embodiment to establish which one of the radiologists MS is closest to patient PAT. In respect to said closest radiologist MS, controller CC then operates as described above so the remaining radiologists are not considered in the optimization.

In an alternate embodiment, if more than one of the radiologists is determined to be within a user-definable critical distance within the ROI position, the FoM as of equation (1) includes for each of those radiologists a separate $FoM_{staff}$ term each with their own priority scaling factor β. In other words, in this multiple radiologist MS embodiment, controller CC operates to negotiate a compromise between the different radiologist positions so as to find one collimator setting that would result in a reasonably long patient-doctor path length for each radiologist within the critical distance so that each radiologist within the critical distance can benefit from a certain degree of secondary radiation SR protection. Said degree varies with the individual distances of the radiologist from the ROI so that the closest one of the radiologist is being assigned a highest priority when considering the optimized collimator setting. In other words, the closer the radiologist to the ROI, the higher his or her priority in considering secondary radiation dosage. In yet other words, controller CC's selection, when operating in multiple radiologists mode, is biased to return an optimized collimator setting so that the respective patient-doctor path length is the longer the closer the radiologist is to the ROI. This embodiment allows using the proposed controller CC in involved interventions that require more than one radiologist.

Figures 4A, 4B:
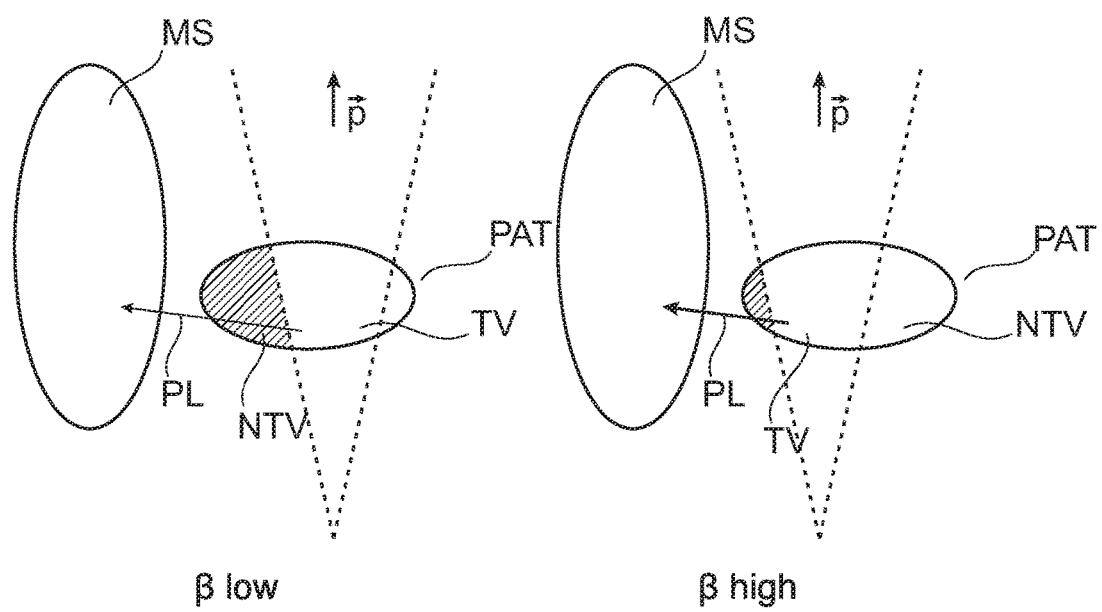
FIG. 4 shows two different collimator settings in side elevation of the imager arrangement of FIG. 1.

FIGS. 4a and 4b are similar to FIG. 3 but show the configuration of FIG. 2 in side elevation rather than FIG. 4's plan view of. The present collimator CC is biased to return a collimator setting akin to FIG. 4a rather than a collimator setting as of FIG. 4b. Similar to the embodiment III) of weight β, the weight β attached to collimator setting in FIG. 4a would be low as compared to weight β attached collimator setting as of FIG. 4b. As can be seen in FIG. 4a a larger part of the patient volume (including the critical area CA) serves as a filter to absorb secondary radiation SR propagating along direction s towards radiologist MS than in the collimator setting of FIG. 4B where there is just a relatively small section of the patient's body that can serve to filter secondary radiation SR. Primary radiation PR dosage for patient however is similar in both cases. PL indicates the different patient-doctor path lengths and the hashured portions show the fractions of patient PAT's body volume that can act as a filter for the secondary radiation SR. In yet other words, a low weight β is used for the FIG. 4a collimator setting because, when using that collimator setting, target volume TV is further removed from staff MS than in the FIG. 4b collimator setting. In FIG. 4a, a larger fraction of patient PAT's body can serve as a secondary radiation SR filter. The FIG. 4a collimator setting is therefore favored by attaching a low β and FIG. b collimator setting is penalized by attaching a high weight β.

Controller CC as proposed herein is biased towards collimator setting solutions where the body fraction as of critical area CA is as large as possible without unduly increasing patient dosage. In other words, the collimator setting as returned by controller CC is required to remain within a pre-definable error margin around the competing collimator that $FoM_{patient}$ would have returned had $FoM_{patient}$ been the sole objective function.

Figure 5:
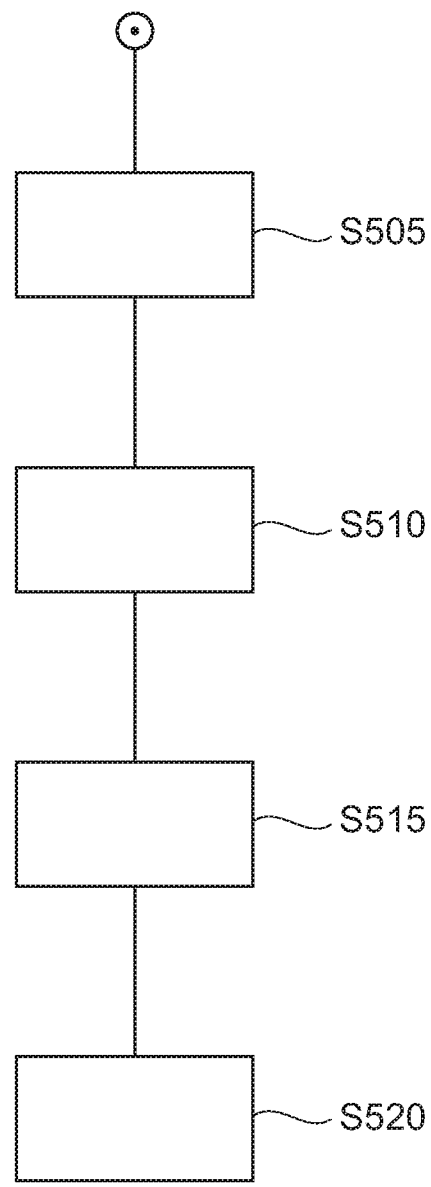
FIG. 5 shows a flow chart for a method of controlling a collimator.

In FIG. 5 there is shown a flow chart for a method of controlling a collimator as proposed herein.

In step S505 a current position of medical staff relative to the patient in the x-ray imager is established. There is also received a coordinate of the region of interest ROI of the patient of which an x-ray image is to be taken.

In step S510 a collimator setting for a collimator in said x-ray imager is selected from a plurality of collimator settings. The selection procedure includes computing a score or a figure of merit of a dosage exposure to patient and medical staff for each of the respective collimator settings. Each collimator setting defines a target volume TV including a region of interest. Said target volume TV also defines a non-target volume NTV. The selection is biased to the collimator settings for which the path length for a secondary radiation from target volume TV through the non-target volume NTV in direction towards the received human operator position is longer than for a competing setting where primary patient dosage is about the same.

In step S515 the so selected or computed collimator setting is forwarded to an x-ray's image collimator and the collimator is set accordingly.

In step S520 a request is issued to confirm the operator's position relative to the patient. If it is established that the position has not changed or has changed but is within a predefined error margin, the current collimator setting as selected at step S510 is maintained. If however it is determined that operator's position has changed relative to the patient, the previous steps S510 to S515 are repeated and an updated collimator position is calculated and the collimator COL is reset accordingly.

The components of controller CC are shown as integrated in one single unit. However in alternative embodiments, some or all components are arranged as separate modules in a distributed architecture and connected in a suitable communication network. Controller CC and its components may be arranged as dedicated FPGAs or as hardwired standalone chips. In some embodiments, controller CC or some of it components are resident in work station CON running as software routines. The components may be programmed in a suitable scientific computing platform such as Matlab® or Simulink® and then translated into C++ or C routines maintained in a library and linked when called on by work station CON.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A collimator controller configured to select, from at least two different collimator settings, a collimator setting for an x-ray imager to acquire an image of an object whilst a person is present at a position around said object, each setting defining
   i) a target volume of the object to be irradiated by a beam of primary radiation generated by an x-ray source of said imager and
   ii) a non-target volume of the object not to be irradiated by said primary radiation beam or to be irradiated at lesser intensity than the target volume,
   the controller's selection biased for the one of the at least two settings that results in a lower secondary radiation dosage for the person that is produced by the interaction of the target volume with the primary radiation, if each of the at least two collimator settings cause about the same dosage for the object when so irradiated,
   the controller further including a detection unit configured to detect the position of the person relative to the object.

2. The controller of claim 1, wherein the controller's selection operation is further based on at least one weight attached to at least one part of the target volume of the object, wherein the weight attached to said at least one part is non-zero, said weight generally reflecting a distance between said part and the position of the person along said line between the reference point of the region of interest and said position, said weight effecting said bias, the so selected collimator setting, when used by the imager, resulting in a lower secondary radiation dosage for the person compared to at least one of the at least one other collimator setting.

3. The controller of claim 1, the detection unit including a position sensor integrated in a badge wearable by the person.

4. The controller of claim 1, the detection unit including at least one actuator device arranged at a predefined position at the imager, the actuator device actuatable by the person to specify that the person's position is substantially equal to said predefined position.

5. The controller of claim 1, the detection unit including a graphical user interface comprising at least one graphical input button associated with a pre-defined position relative to the imager or the object, the button actuatable by the person to specify that the person's position is substantially equal to said predefined position.

6. The controller of claim 1, the detection unit including a range camera operable to sense the operator's position.

7. The controller of claim 2, the controller configured to vary the weight attached to the parts as a function of the detected distance of the person to the object.

8. The controller of claim 2, the controller configured to vary the weight attached to the part as a function of the direction of the primary radiation.

9. A method of controlling a collimator in an x-ray imager to acquire an image of an object, the method comprising acts of:

receiving a position of a person relative to the object;

selecting, from at least two different collimator settings, a collimator setting, each collimator setting defining i) a target volume of the body to be irradiated by a beam of primary radiation generated by an x-ray source of said imager and ii) a non-target volume of the body not to be irradiated by said primary radiation beam or to be irradiated at lesser intensity than the target volume, the selecting operation biased for the one of the at least two settings that results in a lower secondary radiation dosage for the person that is produced by the interaction of the target volume with the primary radiation, if each of the at least two collimator settings cause about the same dosage for the object when so irradiated.

10. An x-ray imager system comprising:

the controller of claim 1;

an X-ray imager having a collimator, a setting of the collimator being selectable by said controller.

11. A non-transitory computer readable medium having stored thereon a program element that configures the controller's selection bias of claim 1.

12. The controller of claim 2, wherein said weight varies exponentially with respect to said distance.

13. The method of claim 9, including:

using the selected collimator setting to control the collimator.

14. The method of claim 9:

responsive to a receiving a new position of the person, updating the collimator setting by selecting a new collimator setting, the selecting operation based on the newly received position.

15. A non-transitory computer readable medium comprising a computer program element for controlling an apparatus, which, when executed by a processing unit configures the processing unit to perform the method of claim 9.

16. A collimator controller configured to select, from at least two different collimator settings, a collimator setting for an x-ray imager to acquire an image of an object whilst a person is present at a position around said object, each setting defining i) a target volume of the object to be irradiated by a beam of primary radiation generated by an x-ray source of said imager and ii) a non-target volume of the object not to be irradiated by said primary radiation beam or to be irradiated at lesser intensity than the target volume, the controller's selection biased for the one of the at least two settings that results in the target volume being more distal to the person along a line between a reference point of a region of interest and the position of the person, if each of the at least two collimator settings cause about the same dosage for the object when so irradiated, the controller further including a detection unit configured to detect the position of the person relative to the object, wherein the controller's selection operation is further based on at least one weight attached to at least one part of the target volume of the object, wherein the weight attached to said at least one part is non-zero, said weight generally reflecting a distance between said part and the position of the person along said line between the reference point of the region of interest and said position, said weight effecting said bias, the so selected collimator setting, when used by the imager, resulting in a lower secondary radiation dosage for the person compared to at least one of the at least one other collimator setting.

17. A collimator controller configured to select, from at least two different collimator settings, a collimator setting for an x-ray imager to acquire an image of an object whilst a person is present at a position around said object, each setting defining i) a target volume of the object to be irradiated by a beam of primary radiation (PR) generated by an x-ray source of said imager and ii) a non-target volume of the object not to be irradiated by said primary radiation beam or to be irradiated at lesser intensity than the target volume, the controller's selection biased for the one of the at least two settings that results in the target volume being more distal to the person along a line between a reference point of a region of interest and the position of the person, if each of the at least two collimator settings cause about the same dosage for the object when so irradiated, the controller further including a detection unit configured to detect the position of the person relative to the object, the detection unit including at least one actuator device arranged at a predefined position at the imager, the actuator device actuatable by the person to specify that the person's position is substantially equal to said predefined position.

\* \* \* \* \*